(12) United States Patent
Herold et al.

(10) Patent No.: US 7,625,893 B2
(45) Date of Patent: Dec. 1, 2009

(54) SUBSTITUTED 4-PHENYL PIPERIDINES FOR USE AS RENIN INHIBITORS

(75) Inventors: Peter Herold, Allschwil (CH); Robert Mah, Allschwil (CH); Stefan Stutz, Allschwil (CH); Vincenzo Tschinke, Allschwil (CH); Aleksandar Stojanovic, Allschwil (CH); Dirk Behnke, Allschwil (CH); Nathalie Jotterand, Allschwil (CH); Stjepan Jelakovic, Allschwil (CH)

(73) Assignee: Speedel Experimenta AG, Allschwil (CH)

( * ) Notice: Subject to any disclaimer, the term of this patent is extended or adjusted under 35 U.S.C. 154(b) by 0 days.

(21) Appl. No.: 12/224,440

(22) PCT Filed: Oct. 3, 2007

(86) PCT No.: PCT/EP2007/060510

§ 371 (c)(1),
(2), (4) Date: Aug. 27, 2008

(87) PCT Pub. No.: WO2008/040764

PCT Pub. Date: Apr. 10, 2008

(65) Prior Publication Data

US 2009/0088426 A1    Apr. 2, 2009

(30) Foreign Application Priority Data

Oct. 4, 2006   (EP) .................. 06121772

(51) Int. Cl.
*C07D 413/12*   (2006.01)
*A61K 31/538*   (2006.01)

(52) U.S. Cl. .................. 514/230.5; 544/105
(58) Field of Classification Search ............ 544/105; 514/230.5
See application file for complete search history.

(56) References Cited

U.S. PATENT DOCUMENTS 5,194,605 A   3/1993   Greenlee et al.

FOREIGN PATENT DOCUMENTS

EP   0 432 975   6/1991

OTHER PUBLICATIONS

International Search Report dated Feb. 28, 2008 in the International (PCT) Application PCT/EP2007/060510 of which the present application is the U.S. National Stage.
PCT Written Opinion dated Feb. 28, 2008 in the International (PCT) Application PCT/EP2007/060510 of which the present application is the U.S. National Stage.

*Primary Examiner*—Kahsay T Habte
(74) *Attorney, Agent, or Firm*—Wenderoth, Lind & Ponack, L.L.P.

(57) ABSTRACT

Compounds of the general formula (I) and the salts thereof, preferably the pharmaceutically acceptable salts thereof; in which $R^1$ is straight-chain $C_{1-8}$-alkanoyloxy, straight-chain $C_{1-8}$-alkoxy, straight-chain $C_{1-8}$-alkoxy-straight-chain-$C_{1-8}$-alkoxy, straight-chain $C_{1-8}$-alkoxycarbonylamino, straight-chain $C_{0-8}$-alkylcarbonylamino, optionally N-mono- or N,N-di-$C_{1-8}$-alkylated amino or hydroxy or straight-chain omega-hydroxy-$C_{1-8}$-alkyl.

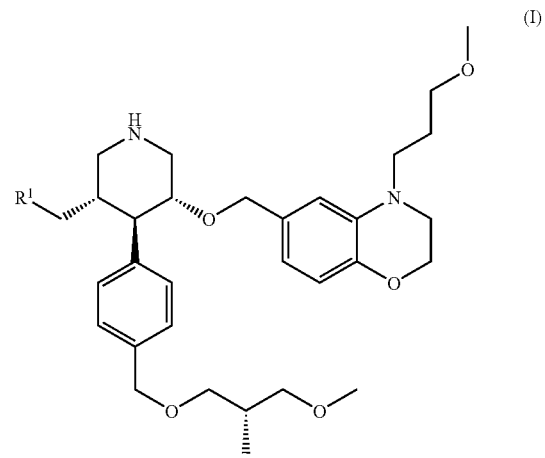

9 Claims, No Drawings

SUBSTITUTED 4-PHENYL PIPERIDINES FOR USE AS RENIN INHIBITORS

The present invention relates to novel substituted 4-phenyl piperidines, to processes for their preparation and to the use of the compounds as medicines, in particular as renin inhibitors.

Piperidine derivatives for use as medicines are known, for example from WO97/09311. However, especially with regard to renin inhibition, there is still a need for highly potent active ingredients. In this context, the improvement of the pharmacokinetic properties is at the forefront. These properties directed towards better bioavailability are, for example, absorption, metabolic stability, solubility or lipophilicity.

The invention therefore provides substituted 4-phenyl piperidines of the general formula

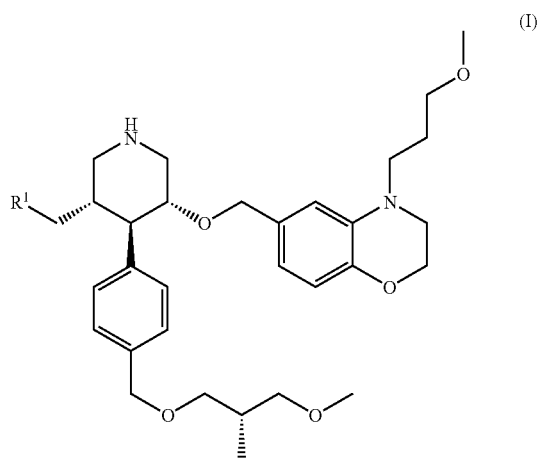

and their salts, preferably their pharmaceutically acceptable salts, in which
$R^1$ is straight-chain $C_{1-8}$-alkanoyloxy, straight-chain $C_{1-8}$alkoxy, straight-chain $C_{1-8}$-alkoxy-straight-chain-$C_{1-8}$- alkoxy, straight-chain $C_{1-8}$alkoxycarbonylamino, straight-chain $C_{0-8}$-alkylcarbonylamino, optionally N-mono- or N,N-di-$C_{1-8}$-alkylated amino or hydroxy or straight-chain omega-hydroxy-$C_{1-8}$-alkyl.

A straight-chain is also sometimes referred to in the literature as linear or un-branched. As used herein, straight-chain $C_{1-8}$alkanoyloxy is straight-chain $C_{0-7}$-alkylcarbonyloxy such as formyloxy, acetyloxy, propionyloxy and butyryloxy. Examples of straight-chain $C_{1-8}$-alkyl are methyl, ethyl, n-propyl, n-butyl, n-pentyl and n-hexyl respectively. Examples of straight-chain omega-hydroxy-$C_{1-8}$-alkyl are hydroxymethyl, 2-hydroxyethyl, 3-hydroxy-n-propyl, 4-hydroxy-n-butyl, 5-hydroxy-n-pentyl and 6-hydroxy-n-hexyl respectively. Examples of straight-chain $C_{1-8}$-alkoxy are radicals such as methoxy, ethoxy, n-propoxy and n-butoxy. Examples of straight-chain $C_0$-$C_8$-alkylcarbonylamino are for example formylamino (formamido), acetylamino, propionylamino and butylcarbonylamino. Optionally N-mono- or N,N-di-$C_{1-8}$-alkylated amino is preferably optionally N-mono- or N,N-di-straight-chain-$C_{1-8}$-alkylated amino and may, for example, be amino, methylamino, dimethylamino, ethylamino, methylethylamino, n-propylamino, n-butylamino, n-pentylamino or n-hexylamino.

Salts are primarily the pharmaceutically usable or nontoxic salts of compounds of formula (I). The term "pharmaceutically useable salts" encompasses salts with inorganic or organic acids, such as hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic acid and the like.

Salts of compounds having salt-forming groups are in particular acid addition salts, salts with bases, or, in the presence of a plurality of salt-forming groups, in some cases also mixed salts or internal salts.

Such salts are formed, for example, from compounds of formula (I) with an acidic group, for example a carboxyl or sulfonyl group, and are, for example, the salts thereof with suitable bases such as non-toxic metal salts derived from metals of group Ia, Ib, IIa and IIb of the Periodic Table of the Elements, for example alkali metal, in particular lithium, sodium, or potassium, salts, alkaline earth metal salts, for example magnesium or calcium salts, and also zinc salts and ammonium salts, including those salts which are formed with organic amines, such as optionally hydroxy-substituted mono-, di- or trialkylamines, in particular mono-, di- or tri(lower alkyl)amines, or with quaternary ammonium bases, e.g. methyl-, ethyl-, diethyl- or triethylamine, mono-, bis- or tris(2-hydroxy(lower alkyl))amines, such as ethanol-, diethanol- or triethanolamine, tris(hydroxymethyl)methylamine or 2-hydroxy-tert-butylamine, N,N-di(lower alkyl)-N-(hydroxy(lower alkyl))amine, such as N,N-di-N-dimethyl-N-(2-hydroxyethyl)amine, or N-methyl-D-glucamine, or quaternary ammonium hydroxides such as tetrabutyl ammoniumhydroxide. The compounds of formula (I) having a basic group, for example an amino group, may form acid addition salts, for example with suitable inorganic acids, e.g. hydrohalic acid such as hydrochloric acid, hydrobromic acid, sulfuric acid with replacement of one or both protons, phosphoric acid with replacement of one or more protons, e.g. ortho-phosphoric acid or metaphosphoric acid, or pyrophosphoric acid with replacement of one or more protons, or with organic carboxylic, sulfonic or phosphonic acids or N-substituted sulfamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, for example the alpha-amino acids mentioned above, and also methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose 6-phosphate, N-cyclohexylsulfamic acid (with formation of the cyclamates) or with other acidic organic compounds such as ascorbic acid. Compounds of formula (I) having acidic and basic groups may also form internal salts.

Salts obtained may be converted to other salts in a manner known per se, acid addition salts, for example, by treating with a suitable metal salt such as a sodium, barium or silver salt, of another acid in a suitable solvent in which an inorganic salt which forms is insoluble and thus separates out of the reaction equilibrium, and base salts by release of the free acid and salt reformation.

The compounds of formula (I), including their salts, may also be obtained in the form of hydrates or include the solvent used for the crystallization.

For the isolation and purification, pharmaceutically unsuitable salts may also find use.

The compounds of formula (I) also include those compounds in which one or more atoms are replaced by their stable, non-radioactive isotopes; for example a hydrogen atom by deuterium.

The compounds of formula (I) have at least three asymmetric carbon atoms and may therefore be in the form of optically pure diastereomers, diastereomeric mixtures, diastereomeric racemates, mixtures of diastereomeric racemates or as meso compounds. The invention encompasses all of these forms. Diastereomeric mixtures, diastereomeric racemates or mixtures of diastereomeric racemates may be separated by customary procedures, for example by column chromatography, thin-layer chromatography, HPLC and the like.

The compounds of formula (I) may also be prepared in optically pure form. The separation into antipodes can be effected by procedures known per se, either preferably at an earlier synthetic stage by salt formation with an optically active acid, for example (+)- or (−)-mandelic acid and separation of the diastereomeric salts by fractional crystallization, or preferably at a relatively late stage by derivatizing with a chiral auxiliary building block, for example (+)- or (−)-camphanoyl chloride, and separation of the diastereomeric products by chromatography and/or crystallization and subsequent cleavage of the bonds to give the chiral auxiliary. The pure diastereomeric salts and derivatives may be analysed to determine the absolute configuration of the piperidine present with common spectroscopic procedures, and X-ray spectroscopy on single crystals constitutes a particularly suitable procedure.

It is possible for the configuration at individual chiral centres in a compound of formula (I) to be inverted selectively. For example, the configuration of asymmetric carbon atoms which bear nucleophilic substituents, such as amino or hydroxyl, may be inverted by second-order nucleophilic substitution, if appropriate after conversion of the bonded nucleophilic substituent to a suitable nucleofugic leaving group and reaction with a reagent which introduces the original substituents, or the configuration at carbon atoms having hydroxyl groups can be inverted by oxidation and reduction, analogously to the process in the European patent application EP-A-0 236 734. Also advantageous is the reactive functional modification of the hydroxyl group and subsequent replacement thereof by hydroxyl with inversion of configuration.

The compound groups mentioned below are not to be regarded as closed, but rather parts of these compound groups may be exchanged with one another or with the definitions given above or omitted in a sensible manner, for example to replace general by more specific definitions. The definitions are valid in accordance with general chemical principles, such as, for example, the common valences for atoms.

The compounds of formula (I) can be prepared in an analogous manner to preparation processes disclosed in the literature. Similar preparation processes are described for example in WO 97/09311. Details of the specific preparation variants can be found in the examples.

A preferred group of compounds of the formula (I) and the salts thereof, preferably the pharmaceutically acceptable salts thereof, are compounds in which
$R^1$ is hydroxy or straight-chain omega-hydroxy-$C_{1-8}$-alkyl, more preferably hydroxy or straight-chain omega-hydroxy-$C_{1-4}$-alkyl.

A further preferred group of compounds of the formula (I) and the salts thereof, preferably the pharmaceutically acceptable salts thereof, are compounds in which
$R^1$ is straight-chain $C_{1-8}$alkoxy or straight-chain $C_{1-8}$alkoxy-straight-chain-$C_{1-8}$-alkoxy, more preferably straight-chain $C_{1-4}$-alkoxy or straight-chain $C_{1-4}$-alkoxy-straight-chain-$C_{1-4}$-alkoxy.

A further preferred group of compounds of the formula (I) and the salts thereof, preferably the pharmaceutically acceptable salts thereof, are compounds in which
$R^1$ is straight-chain $C_{1-8}$alkanoyloxy, more preferably straight-chain $C_{1-4}$-alkanoyloxy.

A further preferred group of compounds of the formula (I) and the salts thereof, preferably the pharmaceutically acceptable salts thereof, are compounds in which
$R^1$ is straight-chain $C_{0-8}$-alkylcarbonylamino, more preferably straight-chain $C_{0-3}$-alkylcarbonylamino.

A further preferred group of compounds of the formula (I) and the salts thereof, preferably the pharmaceutically acceptable salts thereof, are compounds in which
$R^1$ is optionally N-mono- or N,N-di-$C_{1-8}$-alkylated amino, more preferably optionally N-mono- or N,N-di-$C_{1-4}$-alkylated amino.

A further preferred group of compounds of the formula (I) and the salts thereof, preferably the pharmaceutically acceptable salts thereof, are compounds in which
$R^1$ is optionally N-mono- or N,N-di-straight-chain-$C_1$-alkylated amino, more preferably optionally N-mono- or N,N-di-straight-chain-$C_{1-4}$-alkylated amino,.
$R^1$ is very particularly preferably hydroxy, methoxy, 2-methoxy-ethoxy, acetyloxy formamido, methylcarbonylamino or ethylcarbonylamino.

Prodrug derivatives of the compounds described herein are derivatives thereof which on in vivo use liberate the original compound by a chemical or physiological process. A prodrug may for example be converted into the original compound when a physiological pH is reached or by enzymatic conversion. Possible examples of prodrug derivatives are esters of freely available carboxylic acids, S- and O-acyl derivatives of thiols, alcohols or phenols, the acyl group being defined as herein. Preferred derivatives are pharmaceutically acceptable ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters such as lower omega-(amino, mono- or dialkylamino, carboxy, lower alkoxycarbonyl)-alkyl esters or such as lower alpha-(alkanoyloxy, alkoxycarbonyl or dialkylaminocarbonyl)-alkyl esters; conventionally, pivaloyloxymethyl esters and similar esters are used as such.

Because of the close relationship between a free compound, a prodrug derivative and a salt compound, a particular compound in this invention also includes its prodrug derivative and salt form, where this is possible and appropriate.

The compounds of formula (I) and their pharmaceutically acceptable salts have an inhibitory effect on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II raises the blood pressure both directly by arterial constriction, and indirectly by releasing the hormone aldosterone, which retains sodium ions, from the adrenals, which is associated with an increase in the extracellular fluid volume. This increase is attributable to the effect of angiotensin II itself or of the heptapeptide angiotensin III formed therefrom as cleavage product. Inhibitors of the enzymatic activity of renin bring about a reduction in the formation of angiotensin I and, as a consequence thereof, the formation of a smaller amount of angiotensin II. The reduced concentration of this active peptide hormone is the direct cause of the blood pressure-lowering effect of renin inhibitors.

The effect of renin inhibitors is detected inter alia experimentally by means of in vitro tests where the reduction in the formation of angiotensin I is measured in various systems (human plasma, purified human renin together with synthetic or natural renin substrate). The following in vitro test of Nussberger et al. (1987) J. Cardiovascular Pharmacol., Vol. 9, pp. 39-44, is used inter alia. This test measures the formation of angiotensin I in human plasma. The amount of angiotensin I formed is determined in a subsequent radioimmunoassay. The effect of inhibitors on the formation of angiotensin I is tested in this system by adding various concentrations of these substances. The $IC_{50}$ is defined as the concentration of the particular inhibitor which reduces the formation of angiotensin I by 50%. The compounds of the present invention show inhibitory effects in the in vitro systems at minimal concentrations of about $10^{-6}$ to about $10^{-10}$ mol/l.

Illustrative of the invention, the compounds of examples 4 and 5 inhibit the formation of angiotensin I with $IC_{50}$ values in the range of about $1.1$-$3.5 \cdot 10^{-9}$ mol/l.

Renin inhibitors bring about a fall in blood pressure in salt-depleted animals. Human renin differs from renin of other species. Inhibitors of human renin are tested using primates (marmosets, *Callithrix jacchus*) because human renin and primate renin are substantially homologous in the enzymatically active region. The following in vivo test is employed inter alia: the test compounds are tested on normotensive marmosets of both sexes with a body weight of about 350 g, which are conscious, unrestrained and in their normal cages. Blood pressure and heart rate are measured with a catheter in the descending aorta and are recorded radiometrically. Endogenous release of renin is stimulated by combining a low-salt diet for 1 week with a single intramuscular injection of furosemide (5-(aminosulfonyl)-4-chloro-2-[(2-furanylmethyl)amino]benzoic acid) (5 mg/kg). 16 hours after the furosemide injection, the test substances are administered either directly into the femoral artery by means of a hypodermic needle or as suspension or solution by gavage into the stomach, and their effect on blood pressure and heart rate is evaluated. The compounds of the present invention have a blood pressure-lowering effect in the described in vivo test with i.v. doses of about 0.003 to about 0.3 mg/kg and with oral doses of about 0.3 to about 30 mg/kg.

The blood pressure-reducing effect of the compounds described herein can be tested in vivo using the following protocol:

The investigations take place in 5 to 6-week old, male double transgenic rats (dTGR), which overexpress both human angiotensinogen and human renin and consequently develop hypertension (Bohlender J. et al., J. Am. Soc. Nephrol. 2000; 11: 2056-2061). This double transgenic rat strain was produced by crossbreeding two transgenic strains, one for human angiotensinogen with the endogenous promoter and one for human renin with the endogenous promoter. Neither single transgenic strain was hypertensive. The double transgenic rats, both males and females, develop severe hypertension (mean systolic pressure, approximately 200 mm Hg) and die after a median of 55 days if untreated. The fact that human renin can be studied in the rat is a unique feature of this model. Age-matched Sprague-Dawley rats serve as non-hypertensive control animals. The animals are divided into treatment groups and receive test substance or vehicle (control) for various treatment durations. The applied doses for oral administration may range from 0.5 to 100 mg/kg body weight. Throughout the study, the animals receive standard feed and tap water ad libitum. The systolic and diastolic blood pressure, and the heart rate are measured telemetrically by means of transducers implanted in the abdominal aorta, allowing the animals free and unrestricted movement.

The effect of the compounds described herein on kidney damage (proteinuria) can be tested in vivo using the following protocol:

The investigations take place in 4-week old, male double transgenic rats (dTGR), as described above. The animals are divided into treatment groups and receive test substance or vehicle (control) each day for 7 weeks. The applied doses for oral administration may range from 0.5 to 100 mg/kg body weight. Throughout the study, the animals receive standard feed and tap water ad libitum. The animals are placed periodically in metabolism cages in order to determine the 24-hour urinary excretion of albumin, diuresis, natriuresis, and urine osmolality. At the end of the study, the animals are sacrificed and the kidneys and hearts may also be removed for determining the weight and for immunohistological investigations (fibrosis, macrophage/T cell infiltration, etc.).

The pharmacokinetic properties of the compounds described herein can be tested in vivo using the following protocol:

The investigations take place in pre-catheterized (carotid artery) male rats (300 g±20%) that can move freely throughout the study. The compound is administered intravenously and orally (gavage) in separate sets of animals. The applied doses for oral administration may range from 0.5 to 50 mg/kg body weight; the doses for intra-venous administration may range from 0.5 to 20 mg/kg body weight. Blood samples are collected through the catheter before compound administration and over the subsequent 24-hour period using an automated sampling device (AccuSampler, DiLab Europe, Lund, Sweden). Plasma levels of the compound are determined using a validated LC-MS analytical method. The pharmacokinetic analysis is performed on the plasma concentration-time curves after averaging all plasma concentrations across time points for each route of administration. Typical pharmacokinetics parameters to be calculated include: maximum concentration ($C_{max}$), time to maximum concentration ($t_{max}$), area under the curve from 0 hours to the time point of the last quantifiable concentration ($AUC_{0-t}$), area under the curve from time 0 to infinity ($AUC_{0-inf}$), elimination rate constant (K), terminal half-life ($t_{1/2}$), absolute oral bioavailability or fraction absorbed (F), clearance (CL), and Volume of distribution during the terminal phase (Vd).

The compounds of the formula (I) and their pharmaceutically acceptable salts can be used as medicines, e.g. in the form of pharmaceutical compositions. The pharmaceutical compositions can be administered enterally, such as orally, e.g. in the form of tablets, lacquered tablets, sugar-coated tablets, hard and soft gelatine capsules, solutions, emulsions or suspensions, nasally, e.g. in the form of nasal sprays, rectally, e.g. in the form of suppositories, or transdermally, e.g. in the form of ointments or patches. However, administration is also possible parenterally, such as intramuscularly or intravenously, e.g. in the form of solutions for injection.

Tablets, lacquered tablets, sugar-coated tablets and hard gelatine capsules can be produced by processing the compounds of the formula (I) and their pharmaceutically acceptable salts with pharmaceutically inert inorganic or organic excipients.

Excipients of these types which can be used for example for tablets, sugar-coated tablets and hard gelatine capsules are lactose, maize starch or derivatives thereof, talc, stearic acid or salts thereof etc.

Excipients suitable for soft gelatine capsules are, for example, vegetable oils, waxes, fats, semisolid and liquid polyols etc.

Excipients suitable for producing solutions and syrups are, for example, water, polyols, sucrose, invert sugar, glucose etc.

Excipients suitable for solutions for injection are, for example, water, alcohols, polyols, glycerol, vegetable oils, bile acids, lecithin etc.

Excipients suitable for suppositories are, for example, natural or hardened oils, waxes, fats, semiliquid or liquid polyols etc.

The pharmaceutical compositions may in addition comprise preservatives, solubilizers, viscosity-increasing substances, stabilizers, wetting agents, emulsifiers, sweeteners, colorants, aromatizers, salts to alter the osmotic pressure, buffers, coating agents or antioxidants. They may also comprise other substances of therapeutic value.

The present invention further provides the use of the compounds of the formula (I) and their pharmaceutically acceptable salts in the treatment or prevention of high blood pressure, heart failure, glaucoma, myocardial infarction, renal failure and restenoses.

The compounds of the formula (I) and their pharmaceutically acceptable salts can also be administered in combination with one or more agents having cardiovascular activity, e.g. alpha- and beta-blockers such as phentolamine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as aminone, bencyclan, diltiazem, fendiline, flunarizine, nicardipine, nimodipine, perhexyline, verapamil, gallopamil, nifedipine etc.; ACE inhibitors such as cilazapril, captopril, enalapril, lisinopril etc.; potassium activators such as pinacidil; antiserotoninergics such as ketanserine; thromboxane synthetase inhibitors; neutral endopeptidase inhibitors (NEP inhibitors); angiotensin II antagonists; and diuretics such as hydrochlorothiazide, chlorothiazide, acetazolamide, amiloride, bumetanide, benzthiazide, ethacrynic acid, furosemide, indacrinone, metolazone, spironolactone, triamterene, chlorthalidone etc.; sympatholytics such as methyldopa, clonidine, guanabenz, reserpine; and other agents suitable for the treatment of high blood pressure, heart failure or vascular disorders associated with diabetes or renal disorders such as acute or chronic renal failure in humans and animals. Such combinations can be used separately or in products which comprise a plurality of components.

Further substances which can be used in combination with the compounds of formula (I) are the compounds of classes (i) to (ix) on page 1 of WO 02/40007 (and the preferences and examples detailed further therein) and the substances mentioned on pages 20 and 21 of WO 03/027091.

The dosage may vary within wide limits and must of course be adapted to the individual circumstances in each individual case. In general, a daily dose appropriate for oral administration ought to be from about 3 mg to about 3 g, preferably about 10 mg to about 1 g, e.g. approximately 300 mg per adult person (70 kg), divided into preferably 1-3 single doses, which may be for example of equal size, although the stated upper limit may also be exceeded if this proves to be indicated, and children usually receive a reduced dose appropriate for their age and body weight.

EXAMPLES

The following examples illustrate the present invention. All temperatures are stated in degrees Celsius and pressures in mbar. Unless mentioned otherwise, the reactions take place at room temperature. The abbreviation "Rf=xx (A)" means for example that the Rf is found in solvent system A to be xx. The ratio of amounts of solvents to one another is always stated in parts by volume. Chemical names for final products and intermediates have been generated on the basis of the chemical structural formulae with the aid of the AutoNom 2000 (Automatic Nomenclature) program.

HPLC gradients on Hypersil BDS C-18 (5 um); column: 4×125 mm

I 90% water*/10% acetonitrile* to 0% water*/100% acetonitrile* in 5 minutes+2.5 minutes (1.5 ml/min)

II 95% water*/5% acetonitrile* to 0% water*/100% acetonitrile* in 40 minutes (0.8 ml/min)

\* contains 0.1% trifluoroacetic acid

The following abbreviations are used:

Rf ratio of distance migrated by a substance to the distance of the solvent front from the starting point in thin-layer chromatography Rt retention time of a substance in HPLC (in minutes)

m.p. melting point (temperature)

| Nr. | Struktur | Aspect | $R_f$ (System) | Rt (Method) |
|---|---|---|---|---|
| 1 | 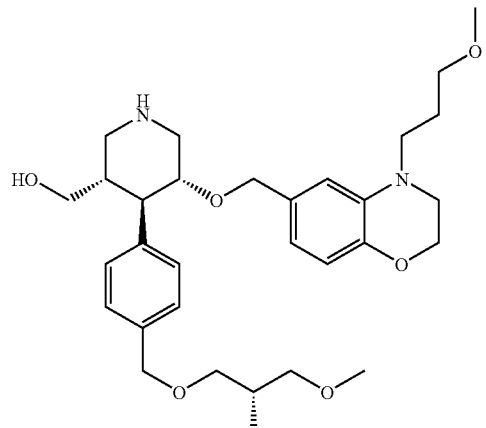 | yellow oil | 0.14 (B) | 3.78 (I) |

-continued

| Nr. | Struktur | Aspect | R$_f$ (System) | Rt (Method) |
|---|---|---|---|---|
| 2 | | light yellow oil | 0.21 (C) | 3.75 (I) |
| 3 | | turbid yellow oil | 0.20 (D) | 3.90 (I) |
| 4 | | yellow oil | 0.28 (A) | 4.21 (I) |

| Nr. | Struktur | Aspect | $R_f$ (System) | Rt (Method) |
|---|---|---|---|---|
| 5 | 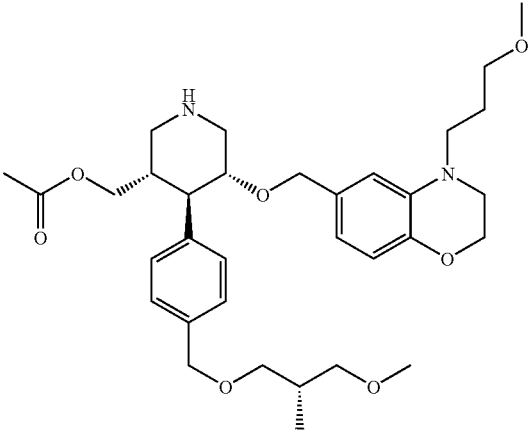 | yellow oil | — | 4.11 (I) |
| 6 | 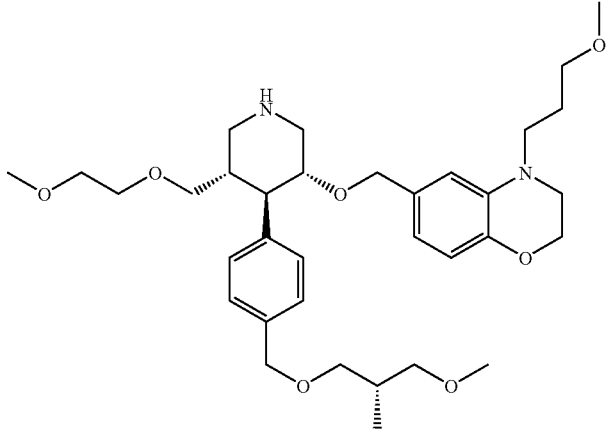 | yellow oil | 0.25 (B) | 4.19 (I) |

Thin-film chromatography eluent systems:
A dichloromethane-methanol-25% ammonia conc.=200: 20:1
B dichloromethane-methanol-25% ammonia conc.=200: 10:1
C dichloromethane-methanol-25% ammonia conc.=200: 30:1
D dichloromethane-methanol-25% ammonia conc.=100: 10:1

General Procedure A: (N-Cbz-deprotection, N-(1-phenyl-ethyl)-deprotection or N-benzyl-deprotection)

To a stirred solution of 1 mmol of "N-protected derivative" in 15 ml of tetrahydrofuran (or methanol) are added 0.1 mmol Pd/C 10% and the reaction mixture is hydrogenated at room temperature. The reaction mixture is filtered and concentrated under reduced pressure. The residue is purified by flash chromatography ($SiO_2$ 60F) to afford the title compound.

General Procedure B: (N-Tos-deprotection)

To a stirred solution of 0.09 mmol "tosylamide" in 10 ml of methanol are added 0.44 mmol sodium dihydrogenphosphate and 0.90 mmol of sodium amalgam (10% Na) at room temperature. The reaction mixture is stirred for 2-18 hours, diluted with water and extracted with ethyl acetate (3×). The organic phases are combined, washed with brine and dried over sodium sulfate. The solvent is concentrated under reduced pressure and the residue is purified by flash chromatography ($SiO_2$ 60F) to afford the title compound.

General Procedure C: ($BH_3$-reduction)

To a stirred solution of 1 mmol of "lactam" in 3 ml of tetrahydrofuran is admixed with 2-4 mmol of borane tetrahydrofuran (1M in tetrahydrofuran) and heated to 50° C. for 2-8 hours.

The reaction mixture is quenched by addition of 10 ml of methanol and concentrated under reduced pressure. The title compound is obtained from the residue by means of flash chromatography ($SiO_2$ 60F).

General Procedure D: (O-alkylation I)

1.2 mmol of sodium hydride (60% dispersion in oil) and 0.1 mmol of tetrabutylammonium iodide are added to a solution of 1 mmol of "alcohol" and 1.1 mmol of "benzyl halide" in 2.0 ml of N,N-dimethylformamide while stirring at −10° C. The reaction mixture is stirred at −10° C. for 1 hour and at room temperature for 18 hours. The mixture is poured into 1M aqueous sodium bicarbonate solution and extracted with tert-butyl methyl ether (2×). The organic phases are washed successively with water and brine, dried with sodium sulfate and evaporated. The title compound is obtained from the residue by means of flash chromatography ($SiO_2$ 60F).

General Method E: (O-alkylation II)

1.1 mmol of sodium hydride (60% dispersion in oil) are added to a solution of 1 mmol of "alcohol" and 1.0-2.0 mmol of "benzyl halide" in 2.0 ml of N,N-dimethylformamide while stirring at −10° C. The reaction mixture is stirred at −10° C. for 1 hour and at room temperature for 18 hours. The mixture is poured into 1M aqueous sodium bicarbonate solution and extracted with tert-butyl methyl ether (2×). The combined organic phases are washed successively with water and brine, dried with sodium sulfate and evaporated. The title compound is obtained from the residue by flash chromatography (SiO₂ 60F).

General Method F: (Alcohol Desilylation)

A solution of 1 mmol of "silyl ether" in 5 ml of tetrahydrofuran is mixed with 1.5-2.0 mmol of tetrabutylammonium fluoride (1M solution in tetrahydrofuran) and the solution is stirred at room temperature for 1-2 hours. The reaction solution is then diluted with water and extracted with tert-butyl methyl ether (2×). The combined organic phases are dried with sodium sulfate and evaporated. The title compound is obtained from the residue by flash chromatography (SiO₂ 60F).

Example 1

{(3S,4R,5R)-4-[4-((S)-3-Methoxy-2-methyl-propoxymethyl)-phenyl]-5-[4-(3-methoxy -propyl)-3,4-dihydro-2H-benzo[1,4]oxazin-6-ylmethoxy]-piperidin-3-yl}-methanol According to general procedure A, (3S,4R,5R)-3-hydroxymethyl-4-[4-((S)-3-methoxy-2-methyl-propoxymethyl)-phenyl]-5-[4-(3-methoxy-propyl)-3,4-dihydro-2H-benzo [1,4]oxazin-6-ylmethoxy]-piperidine-1-carboxylic acid benzyl ester is used to afford the title compound.

The starting material(s) is(are) prepared as follows:

a) (3S,4R,5R)-3-Hydroxymethyl-4-[4-((S)-3-methoxy-2-methyl-propoxymethyl) -phenyl]-5-[4-(3-methoxy-propyl)-3,4-dihydro-2H-benzo[1,4]oxazin-6-ylmethoxyl]-piperidine-1-carboxylic acid benzyl ester According to general procedure C, (3S,4R,5R)-3-hydroxymethyl-4-[4-((S)-3-methoxy-2-methyl-propoxymethyl)-phenyl]-5-[4-(3-methoxy-propyl)-3-oxo-3,4-dihydro-2H-benzo[1,4]oxazin-6-ylmethoxy]-piperidine-1-carboxylic acid benzyl ester is used to afford the title compound as a turbid oil. Rf=0.15 (EtOAc-heptane 2:1); Rt=5.22 (gradient I).

b) (3S,4R,5R)-3-Hydroxymethyl-4-[4-((S)-3-methoxy-2-methyl-propoxymethyl) -phenyl]-5-[4-(3-methoxy-propyl)-3-oxo-3,4-dihydro-2H-benzo[1,4]oxazin-6-ylmethoxy]-piperidine-1-carboxylic acid benzyl ester A solution of 8.526 mmol of (3R,4R,5S)-4-[4-((S)-3-methoxy-2-methyl-propoxymethyl) -phenyl]-3-[4-(3-methoxy-propyl)-3-oxo-3,4-dihydro-2H-benzo [1,4]oxazin-6-ylmethoxy]-5-trityloxymethyl-piperidine-1-carboxylic acid benzyl ester in 20 ml of tetrahydrofuran and 80 ml of methanol is treated with 12.789 mmol of toluene-4-sulfonic acid-.monohydrate. After stirring for 15 hours, the reaction mixture is basified with saturated aqueous sodium bicarbonate solution and concentrated under reduced pressure to remove most of the methanol and tetrahydrofuran. The residue is extracted with dichloromethane (3×)—the combined organic layers are washed successively with water and brine, dried with sodium sulfate and evaporated. The title compound is obtained as a yellow oil from the residue by flash chromatography (SiO₂ 60F). Rt=4.86 (gradient I).

c) (3R,4R,5S-4-[4-((S)-3-Methoxy-2-methyl-propoxymethyl)-phenyl]-3-[4-(3-methoxy-propyl)-3-oxo-3,4-dihydro-2H-benzo[1,4]oxazin-6-ylmethoxy]-5-trityloxymethyl-piperidine-1-carboxylic acid benzyl ester According to general procedure D, (3R,4R,5S)-3-hydroxy-4-[4-((S)-3-methoxy-2-methyl-propoxymethyl)-phenyl]-5-trityloxymethyl-piperidine-1-carboxylic acid benzyl ester and 6-chloromethyl-4-(3-methoxy-propyl)-4H-benzo [1,4]oxazin-3-one [857272-02-7] are used to afford the title compound as a yellow oil. Rt=6.58 (gradient I).

d) (3R,4R,5S)-3-Hydroxy-4-[4-((S)-3-methoxy-2-methyl-propoxymethyl)-phenyl]-5-trityloxymethyl-piperidine-1-carboxylic acid benzyl ester 8.478 mmol of benzyl chloroformate are added dropwise to a mixture of 8.478 mmol of (3R,4R,5S)-4-[4-((S)-3-methoxy-2-methyl-propoxymethyl)-phenyl]-5-trityloxy -methyl-piperidin-3-ol (L)-(+)-mandelate in 150 ml of ethyl acetate and 150 ml of saturated aqueous sodium bicarbonate solution at 0° C. After 1 hour, the reaction mixture is partitioned between saturated aqueous sodium carbonate solution and ethyl acetate—the organic layer is washed successively with water and brine. The combined aqueous layers are back-extracted with ethyl acetate—the combined organic layers are dried with sodium sulfate and evaporated. The crude title compound is obtained as a white foam. Rt=6.14 (gradient I).

e) (3R,4R,5S)-4-[4-((S)-3-Methoxy-2-methyl-propoxymethyl)-phenyl]-5-trityloxymethyl-piperidin-3-ol (L)-(+)-mandelate According to general procedure A, (3R,4R,5S)-1-benzyl-4-[4-((S)-3-methoxy-2-methyl-propoxymethyl)-phenyl]-5-trityloxymethyl-piperidin-3-ol (L)-(+)-mandelate is used to afford the title compound as a white foam. Rt=4.92 (gradient I).

f) (3R,4R,5S)-1-Benzyl-4-[4-((S)-3-methoxy-2-methyl-propoxymethyl)-phenyl]-5-trityloxymethyl-piperidin-3-ol (L)-(+)-mandelate 2.36 mmol of (L)-(+)-mandelic acid are added to a solution of 5.90 mmol of (rac-3R,4R,5S)-1-benzyl-4-[4-((S)-3-methoxy-2-methyl-propoxymethyl)-phenyl]-5-trityloxymethyl-piperidin-3-ol in 36 ml of tetrahydrofuran at 60° C. (oil bath temperature). 36 ml of n-hexane are slowly added dropwise at 60° C. The mixture is slowly cooled to room temperature over the course of 3 hours and, after a brief treatment in an ultrasonic bath, then cooled at 0° C. for 2 hours. The precipitate is filtered off and washed with 1:4 tetrahydrofuran/n-hexane to afford the title compound as a white solid. Rt=5.36 (gradient I).

For analytical purposes, a small amount of the salt is dissolved in ethyl acetate and washed with saturated aqueous sodium carbonate solution (2×). The organic phase is washed with brine, dried with sodium sulfate and evaporated to afford the title compound as the free base (white solid). HPLC;

Rt=12.81 (Daicel Chiralpak AD 0.46×25 cm; 95% hexane/ 5% isopropanol; 0.7 ml/minute for 60 minutes).

g) (rac-3R,4R,5S)-1-Benzyl-4-[4-((S)-3-methoxy-2-methyl-propoxymethyl)-phenyl]-5-trityloxymethyl-piperidin-3-ol 86.852 mmol of a solution of borane-tetrahydrofuran (1M/ THF) are added dropwise to a solution of 43.426 mmol of 1-benzyl-4-[4-((S)-3-methoxy-2-methyl-propoxy -methyl)-phenyl]-3-(R,S)-trityloxymethyl-1,2,3,6-tetrahydro-pyridine in 220 ml of tetrahydrofuran at room temperature. After overnight stirring, the reaction mixture is cooled to 10° C. and successively treated dropwise with a solution of 251.871 mmol of potassium hydroxide in 60 ml of water and then with 86.852 mmol of hydrogen peroxide (30%/water). The reaction mixture is slowly warmed to 65° C., stirred for 3 hours and then re-cooled to room temperature. The reaction mixture is partitioned between tert-butyl methyl ether and ice-water—the organic layer is washed with brine. The combined aqueous layers are extracted with tert-butyl methyl ether (2×)—the combined organic layers are dried with sodium sulfate and evaporated. The residue is purified by flash chromatography ($SiO_2$ 60F) to afford the title compound as a yellow oil. Rf=0.15 (EtOAc-heptane 1:1); Rt=5.36 (gradient I).

h) 1-Benzyl-4-[4-((S)-3-methoxy-2-methyl-propoxymethyl)-phenyl]-3-(R,S) -trityloxymethyl-1,2,3,6-tetrahydro-pyridine 102.636 mmol of thionyl chloride are slowly added to a solution of 85.53 mmol of 1-benzyl-4-[4-((S)-3-methoxy-2-methyl-propoxymethyl)-phenyl]-3-(R,S)-trityloxymethyl - piperidin-4-(R,S)-ol in 250 ml of pyridine at 0° C., taking care that the internal temperature stays below 10° C. After 5 minutes, the reaction mixture is quenched by adding 50 ml of 4N NaOH solution and concentrated under reduced pressure. The residue is dissolved in ethyl acetate and washed successively with saturated aqueous sodium bicarbonate solution, water and brine, dried with sodium sulfate and evaporated. The residue is purified by flash chromatography ($SiO_2$ 60F) to afford the title compound as a yellow oil. Rf=0.28 (EtOAc-heptane-25% ammonia conc. 100:200:1); Rt=5.64 (gradient I).

i) 1-Benzyl-4-[4-((S)-3-methoxy-2-methyl-propoxymethyl)-phenyl]-3-(R,S) -trityloxymethyl-piperidin-4-(R,S)-ol 2.32 mmol of 1,2-dibromoethane are added to a suspension of 156.518 mmol of magnesium in 20 ml of tetrahydrofuran under argon at room temperature. The reaction mixture is warmed until the magnesium starts to react and then 3 ml of a solution of 151.509 mmol of 1-bromo-4-((S)-3-methoxy-2-methyl-propoxymethyl)-benzene in 170 ml of tetrahydrofuran, followed by the rest of the solution, is added while maintaining a gentle reflux. After 2 hours, the reaction mixture is cooled to room temperature and then a solution of 125.214 mmol of 1-benzyl-3-trityloxymethyl -piperidin-4-one [234757-27-8] in 170 ml of tetrahydrofuran is slowly added, taking care to keep the internal reaction temperature under 40° C. After overnight stirring at room temperature, the reaction mixture is quenched with saturated aqueous ammonium chloride solution. Ethyl acetate is added to the reaction mixture and the phases separated—the organic phase is washed successively with water and brine. The combined aqueous phases are back-extracted with ethyl acetate—the combined organic phases are dried with sodium sulfate and evaporated. The residue is purified by flash chromatography ($SiO_2$ 60F) to afford the title compound as a yellow oil. Rf=0.30 (EtOAc-heptane-25% ammonia conc. 100:100:1); Rt=5.43 (gradient I).

j) 1-Bromo-4-((S)-3-methoxy-2-methyl-propoxymethyl)-benzene

According to general method E, 1-bromo-4-chloromethyl-benzene [589-17-3] and (R)-3-methoxy-2-methyl-propan-1-ol are used to afford the title compound as a yellow oil. Rf=0.44 (EtOAc-heptane 1:6); Rt=5.29 (gradient I).

k) (R)-3-Methoxy-2-methyl-propan-1-ol

According to general method F, triisopropyl-(3-methoxy-2(S)-methylpropoxy)silane is used to afford the title compound as a yellow oil. Rf=0.42 (dichloromethane-diethyl-ether 1:1).

l) Triisopropyl-((S)-3-methoxy-2-methylpropoxy)silane 3.09 g of sodium hydride (60% dispersion in oil) are added to a solution of 9.55 g of (S)-2-methyl-3-triisopropylsilanyloxypropan-1-ol [256643-28-4] and 7.3 ml of methyl iodide in 70 ml of N,N-dimethylformamide at 0° C. After 60 hours at room temperature, the reaction mixture is diluted with tert-butyl methyl ether and washed successively with water and brine, dried with sodium sulfate and evaporated. The residue is purified by flash chromatography ($SiO_2$ 60F) to afford the title as a yellow oil. Rf=0.51 (EtOAc-heptane 1:10).

Example 2

N-{(3S,4R,5R)-4-[4-((S)-3-Methoxy-2-methyl-propoxymethyl)-phenyl]-5-[4-(3-methoxy-propyl)-3,4-dihydro-2H-benzo[1,4]oxazin-6-ylmethoxy]-piperidin-3-ylmethyl}-acetamide According to general procedure A, (3R,4R,5R)-3-(acetylamino-methyl)-4-[4-((S)-3-methoxy-2-methyl-propoxymethyl)-phenyl]-5-[4-(3-methoxy-propyl)-3,4-dihydro-2H -benzo[1,4]oxazin-6-ylmethoxy]-piperidine-1-carboxylic acid benzyl ester is used to afford the title compound.

The starting material(s) is(are) prepared as follows:

a) (3R,4R,5R)-3-(Acetylamino-methyl)-4-[4-((S)-3-methoxy-2-methyl -propoxymethyl)-phenyl]-5-[4-(3-methoxy-propyl)-3,4-dihydro-2H -benzo[1,4]oxazin-6-ylmethoxy]-piperidine-1-carboxylic acid benzyl ester 5.936 mmol of acetyl chloride are added to a solution of 5.396 mmol of (3R,4R,5R)-3-aminomethyl-4-[4-((S)-3-methoxy-2-methyl-propoxymethyl)-phenyl]-5-[4-(3-methoxy -propyl)-3,4-dihydro-2H-benzo[1,4]oxazin-6-ylmethoxy]-piperidine-1-carboxylic acid benzyl ester and 6.475 mmol of triethylamine in 80 ml of dichloromethane under argon at 0° C. After 30 minutes, the reaction mixture is quenched with saturated aqueous sodium bicarbonate solution and extracted with tert-butyl methyl ether (2×). The combined organic layers are washed successively with water and brine, dried with sodium sulfate and evaporated. The residue is purified by flash chromatography (SiO$_2$ 60F) to afford the title compound as a yellow oil. Rt=4.98 (gradient I).

b) (3R,4R,5R)-3-Aminomethyl-4-[4-((S)-3-methoxy-2-methyl-propoxymethyl) -phenyl]-5-[4-(3-methoxy-propyl)-3,4-dihydro-2H-benzo[1,4]oxazin-6-ylmethoxy]-piperidine-1-carboxylic acid benzyl ester 7.128 mmol of triphenylphosphine are added to a solution of 5.940 mmol of (3S,4R,5R)-3-azidomethyl-4-[4-((S)-3-methoxy-2-methyl-propoxymethyl)-phenyl]-5-[4-(3-methoxy-propyl)-3,4-dihydro-2H-benzo[1,4]oxazin-6-yl-methoxy]-piperidine-1-carboxylic acid benzyl ester in 20 ml of methanol, 20 ml of tetrahydrofuran, 5 ml of water and 3.56 ml of concentrated aqueous ammonia (25%) at room temperature. After overnight stirring, the reaction mixture is partitioned between tert-butyl methyl ether and 5:1 water/saturated aqueous sodium bicarbonate solution. The aqueous layer is extracted with tert-butyl methyl ether—the combined organic layers are washed successively with water and brine, dried with sodium sulfate and evaporated. The residue is purified by flash chromatography (SiO$_2$ 60F) to afford the title compound as a yellow oil. Rf=0.42 (dichloromethane-methanol-25% ammonia conc. 200:20:1); Rt=4.64 (gradient I).

c) (3S,4R,5R)-3-Azidomethyl-4-[4-((S)-3-methoxy-2-methyl-propoxymethyl)-phenyl]-5-[4-(3-methoxy-propyl)-3,4-dihydro-2H-benzo[1,4]oxazin-6-yl-methoxy]-piperidine-1-carboxylic acid benzyl ester 31.265 mmol of sodium azide are added to a solution of 6.253 mmol of (3R,4R,5S)-4-[4-((S)-3-methoxy-2-methyl-propoxymethyl)-phenyl]-3-[4-(3-methoxy-propyl)-3,4-dihydro-2H-benzo[1,4]oxazin-6-ylmethoxy]-5-(toluene-4-sulfonyloxymethyl) -piperidine-1-carboxylic acid benzyl ester in 50 ml of 1,3-dimethyl-tetrahydro -pyrimidin-2-one (DMPU) under argon at 45° C. After 5 hours, the reaction mixture is cooled to room temperature, diluted with tert-butyl methyl ether, washed with water and brine, dried with sodium sulfate and evaporated. The crude title compound is obtained as a yellow oil. Rf=0.58 (EtOAc-heptane 2:1); Rt=5.96 (gradient I).

d) (3R,4R,5S)-4-[4-((S)-3-Methoxy-2-methyl-propoxymethyl)-phenyl]-3-[4-(3-methoxy-propyl)-3,4-dihydro-2H-benzo[1,4]oxazin-6-ylmethoxy]-5-(toluene-4-sulfonyloxymethyl)-piperidine-1-carboxylic acid benzyl ester 7.077 mmol of 4-methyl-benzenesulfonyl chloride are added to a solution of 6.583 mmol of (3S,4R,5R)-3-hydroxymethyl-4-[4-((S)-3-methoxy-2-methyl-propoxymethyl) -phenyl]-5-[4-(3-methoxy-propyl)-3,4-dihydro-2H-benzo[1,4]oxazin-6-ylmethoxy]-piperidine-1-carboxylic acid benzyl ester (Example 1a), 9.875 mmol of triethylamine and 0.329 mmol of dimethyl-pyridin-4-yl-amine in 65 ml of dichloromethane under argon at 0° C. After overnight stirring at room temperature, the reaction mixture is diluted with tert-butyl methyl ether, washed successively with saturated aqueous sodium bicarbonate solution, water and brine, dried with sodium sulfate and evaporated. The crude title compound is obtained as a yellow oil. Rf=0.44 (EtOAc-heptane 2:1); Rt=5.94 (gradient I).

According to the procedures described in example 2, the following compounds are prepared in an analogous manner:

3 N-{(3S,4R,5R)-4-[4-((S)-3-Methoxy-2-methyl-propoxymethyl)-phenyl]-5-[4-(3-methoxy-propyl)-3,4-dihydro-2H-benzo[1,4]oxazin-6-ylmethoxy]-piperidin-3-ylmethyl}-propionamide using propionyl chloride instead of acetyl chloride in step a.

7 N-{(3S,4R,5R)-4-[4-((S)-3-Methoxy-2-methyl-propoxymethyl)-phenyl]-5-[4-(3-methoxy-propyl)-3,4-dihydro-2H-benzo[1,4]oxazin-6-ylmethoxy]-piperidin-3-ylmethyl}-formamide replacing step a with the following procedure:

1.4 mmol of 4-nitrophenylformiate are added to a solution of 1 mmol of (3R,4R,5R)-3-aminomethyl-4-[4-((S)-3-methoxy-2-methyl-propoxymethyl)-phenyl]-5-[4-(3-methoxy - propyl)-3,4-dihydro-2H-benzo[1,4]oxazin-6-ylmethoxy]-piperidine-1-carboxylic acid benzyl ester (example 2b) in 10 ml of dichloromethane under argon followed by the addition of 1 mmol of triethylamine. After 60 minutes, the reaction mixture is evaporated. The residue is purified by flash chromatography (SiO$_2$ 60F) to afford the title compound, which is identified based on the Rf value.

Example 4

6-{(3R,4R,5S)-5-Methoxymethyl-4-[4-((S)-3-methoxy-2-methyl-propoxymethyl) -phenyl]-piperidin-3-yloxymethyl}-4-(3-methoxy-propyl)-3,4-dihydro-2H -benzo[1,4]oxazine According to general procedure A, (3S,4R,5R)-3-methoxymethyl-4-[4-((S)-3-methoxy-2-methyl-propoxymethyl)-phenyl]-5-[4-(3-methoxy-propyl)-3,4-dihydro-2H -benzo[1,4]oxazin-6-ylmethoxy]-piperidine-1-carboxylic acid benzyl ester is used to afford the title compound.

The starting material(s) is(are) prepared as follows:

a) (3S,4R,5R)-3-Methoxymethyl-4-[4-((S)-3-methoxy-2-methyl-propoxymethyl) -phenyl]-5-[4-(3-methoxy-propyl)-3,4-dihydro-2H-benzo[1,4]oxazin-6-ylmethoxy]-piperidine-1-carboxylic acid benzyl ester 2.568 mmol of methyl iodide are added to a suspension of 0.642 mmol of (3S,4R,5R)-3-hydroxymethyl-4-[4-((S)-3-methoxy-2-methyl-propoxymethyl)-phenyl]-5-[4-(3-methoxy-propyl)-3,4-dihydro-2H-benzo[1,4]oxazin-6-yl-methoxy]-piperidine-1-carboxylic acid benzyl ester (Example 1a) and 0.963 mmol of sodium hydride (60% dispersion in oil) under argon at 0° C. After stirring for 1 hour at 0° C. and 1 hour at room temperature, the reaction mixture is partitioned between tert-butyl methyl ether and saturated aqueous sodium bicarbonate solution. The aqueous layer is extracted with tert-butyl methyl ether (2×)—the combined organic layers are washed successively with water and brine, dried with sodium sulfate and evaporated. The residue is purified by flash chromatography (SiO$_2$ 60F) to afford the title compound as a yellow oil. Rf=0.41 (EtOAc-heptane 1:1); Rt=5.87 (gradient I).

According to the procedures described in example 4, the following compound is prepared in an analogous manner:

6 6-{(3R,4R,5S)-5-(2-Methoxy-ethoxymethyl)-4-[4-((S)-3-methoxy-2-methyl-propoxymethyl)-phenyl]-piperidin-3-yloxymethyl}-4-(3-methoxy-propyl)-3,4-dihydro-2H-benzo[1,4]oxazine using 1-bromo-2-methoxy-ethane (instead of methyl iodide) and 1 equivalent of tetrabutylammonium iodide in step a.

Example 5
Acetic acid (3S,4R,5R)-4-[4-((S)-3-methoxy-2-methyl-propoxymethyl)-phenyl]-5-[4-(3-methoxy-propyl)-3,4-dihydro-2H-benzo[1,4]oxazin-6-yl-methoxy]-piperidin-3-ylmethyl ester According to general procedure A, (3S,4R,5R)-3-acetoxymethyl-4-[4-((S)-3-methoxy-2-methyl-propoxymethyl)-phenyl]-5-[4-(3-methoxy-propyl)-3,4-dihydro-2H-benzo[1,4]oxazin-6-ylmethoxy]-piperidine-1-carboxylic acid benzyl ester is used to afford the title compound.

The starting material(s) is(are) prepared as follows:

a) (3S,4R,5R)-3-Acetoxymethyl-4-[4-((S)-3-methoxy-2-methyl-propoxymethyl)-phenyl]-5-[4-(3-methoxy-propyl)-3,4-dihydro-2H-benzo[1,4]oxazin-6-ylmethoxy]-piperidine-1-carboxylic acid benzyl ester Analogously to Example 2a, (3S,4R,5R)-3-hydroxymethyl-4-[4-((S)-3-methoxy-2-methyl-propoxymethyl)-phenyl]-5-[4-(3-methoxy-propyl)-3,4-dihydro-2H -benzo[1,4]oxazin-6-ylmethoxy]-piperidine-1-carboxylic acid benzyl ester (Example 1a) and acetyl chloride are used to afford the title compound as a colorless oil. Rf=0.20 (EtOAc-heptane 1:1); Rt=5.69 (gradient I).

The invention claimed is:
1. A compound of the formula (I)

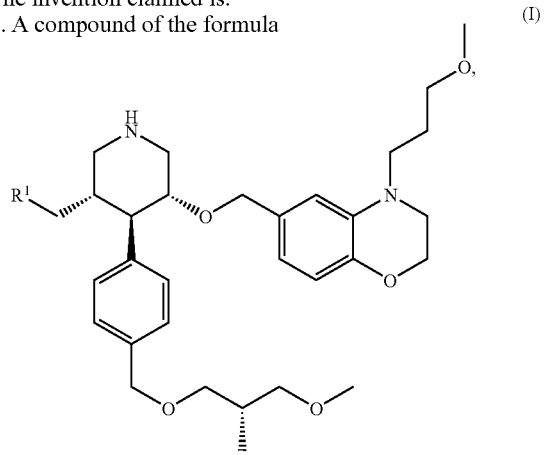

or its pharmaceutically acceptable salt, in which $R^1$ is straight-chain $C_{1-8}$-alkanoyloxy, straight-chain $C_{1-8}$-alkoxy, straight-chain $C_{1-8}$-alkoxy-straight-chain-$C_{1-8}$-alkoxy, straight-chain $C_{1-8}$-alkoxycarbonylamino, straight-chain $C_{0-8}$-alkylcarbonylamino, optionally N-mono- or N,N-di-$C_{1-8}$-alkylated amino or hydroxy or straight-chain omega-hydroxy-$C_{1-8}$-alkyl.

2. A compound or its pharmaceutically acceptable salt according to claim1 1, in which $R^1$ is hydroxy or straight-chain omega-hydroxy-$C_{1-8}$-alkyl.

3. A compound or its pharmaceutically acceptable salt according to claim 1, in which $R^1$ is straight-chain $C_{1-8}$-alkoxy or straight-chain $C_{1-8}$-alkoxy-straight-chain-$C_{1-8}$-alkoxy.

4. A compound or its pharmaceutically acceptable salt according to claim 1, in which $R^1$ is straight-chain $C_{1-8}$-alkanoyloxy.

5. A compound or its pharmaceutically acceptable salt according to claim 1, in which $R^1$ is straight-chain $C_{0-8}$-alkylcarbonylamino.

6. A compound or its pharmaceutically acceptable salt according to claim 1, in which $R^1$ is optionally N-mono- or N,N-di-straight-chain-$C_{1-8}$-alkylated amino.

7. A compound or its pharmaceutically acceptable salt according to claim 1, in which $R^1$ is hydroxy, methoxy, 2-methoxy-ethoxy, acetyloxy, formamido, methylcarbonylamino or ethylcarbonylamino.

8. A pharmaceutical composition comprising a compound or its pharmaceutically acceptable salt according to claim 1 and a pharmaceutically inert inorganic or organic excipient.

9. A method for the treatment of high blood pressure, glaucoma, and myocardial infarction, which comprises administering a therapeutically effective amount of a compound or its pharmaceutically acceptable salt according to claim 1 to a person in need thereof.

* * * * *